United States Patent [19]

Vishnuvajjala

[11] Patent Number: 4,658,047

[45] Date of Patent: Apr. 14, 1987

[54] METHOD OF PREPARING 1,2-DIAMINOCYCLOHEXANE TETRACHLORO PLATINUM (IV) ISOMERS

[75] Inventor: Babu R. Vishnuvajjala, Rockville, Md.

[73] Assignee: The United States of America as represented by the Department of Health and Human Services, Washington, D.C.

[21] Appl. No.: 780,932

[22] Filed: Sep. 27, 1985

[51] Int. Cl.$^4$ .............................................. C07F 15/00
[52] U.S. Cl. ..................................................... 556/137
[58] Field of Search ........................................ 556/137

[56] References Cited

U.S. PATENT DOCUMENTS

| | | | |
|---|---|---|---|
| Re. 30,971 | 6/1982 | Tobe et al. ......................... | 556/137 |
| 4,115,418 | 9/1978 | Gale et al. . | |
| 4,119,653 | 10/1978 | Tobe et al. . | |
| 4,119,654 | 10/1978 | Tobe et al. . | |
| 4,140,707 | 2/1979 | Cleare et al. ....................... | 556/137 |
| 4,169,846 | 10/1979 | Kidani et al. . | |
| 4,177,263 | 12/1979 | Rosenberg et al. . | |
| 4,182,724 | 1/1980 | Tobe et al. ......................... | 556/137 |
| 4,284,579 | 8/1981 | Meischen et al. . | |
| 4,329,299 | 5/1982 | Hydes ................................. | 556/137 |
| 4,431,666 | 2/1984 | Bulten et al. . | |
| 4,466,924 | 8/1984 | Verbeck et al. . | |
| 4,482,569 | 11/1984 | Bulten et al. . | |
| 4,550,187 | 10/1985 | Anderson et al. ................. | 556/137 |
| 4,599,352 | 7/1986 | Narayanan et al. ............ | 556/137 X |

OTHER PUBLICATIONS

Chemical Abstracts 88 16014k (1978).

*Primary Examiner*—Helen M. S. Sneed
*Attorney, Agent, or Firm*—John S. Roberts, Jr.

[57] ABSTRACT

The present invention is a method of preparing tetrachlorodiamine cyclohexane platinum (IV) by reacting a diamine selected from the group consisting of 1,2-diaminocyclohexane and operable isomers thereof in the form of a dihydrohalide with alkali metal or hydrogen hexachloroplatinate. The preferred hexachloroplatinate is potassium salt and the isomers utilized from the diamine are selected from the group consisting of cis, trans (d,l), trans-l, and trans-d. The process noted is where the 1,2-diaminocyclohexane is used in about equimolar amounts with hexachloroplatinate which is subjected to heating at reflux temperature for 12–24 hours in aqueous solvent, cooled and filtered.

6 Claims, No Drawings

METHOD OF PREPARING 1,2-DIAMINOCYCLOHEXANE TETRACHLORO PLATINUM (IV) ISOMERS

The present invention is a method of preparing tetrachlorodiamine cyclohexane platinum (IV) by reacting a diamine selected from the group consisting of 1,2-diaminocyclohexane and operable isomers thereof in the form of a dihydrohalide with alkali metal or hydrogen hexachloroplatinate The preferred hexachloroplatinate is potassium salt and the isomers utilized from the diamine are selected from the group consisting of cis, trans (d,l), trans-l and trans-d The process noted is where the 1,2-diaminocyclohexane is used in about equimolar amounts with hexachloroplatinate which is subjected to heating at reflux temperature for 12–24 hours in aqueous solvent, cooled and filtered The process of the present invention is illustrated by Scheme I below:

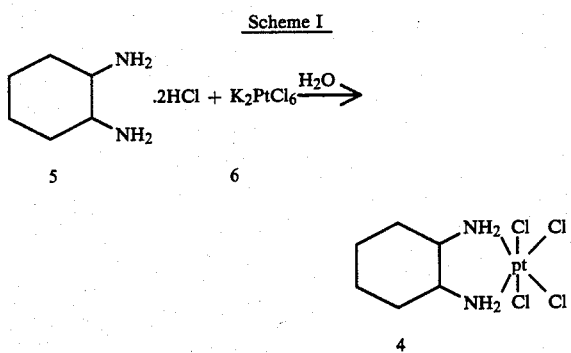

The present utility of compounds resulting from the process claims can scarcely be questioned. Similar platinum compounds have proved useful in the National Cancer Institute anti-cancer program during the past several years. One basic patent is Rosenberg U.S. Pat. No. 4,177,263 which notes the simple amino complexes with platinum termed cisplatin and researchers since that time have endeavored to fill the gap where utilization of cisplatin is shown that tumor cells have acquired resistance to this compound.

The platinum compounds developed so far have been divided into Pt-IV and Pt-II and the process of producing the present compounds is of the IV variety The products, as well as the isomeric products, produced from the present method are known The isomeric products may be produced, S. Saito, *Chem. Lett.*, Vol. 123, 1976, and Whitney, *J. Org. Chem.*, 45:4214, 1980. As noted previously, the isomers involved are cis, trans (d,l), trans-l and trans-d. These isomers in the cisplatin-II system have been described in U.S. Pat. No.4,169,846 Kidani.

MATERIAL INFORMATION DISCLOSURE

Related products and accompanying processes are described in the following patents:

U.S. Pat. No. 4,177,263 Rosenberg et al—cisplatin

U.S. Pat. No. 4,169,846 Kidani et al—stereoisomerism of 1,2-diaminocyclohexane and particularly the cis, trans-d or trans-l isomers.

U.S. Pat. No. 4,115,418 Gale et al

U.S. Pat. No. 4,119,653 Tobe et al

U.S. Pat. No. 4,119,654 Tobe et al—platinum IV compound

U.S. Pat. No. 4,284,579 Meischen et al—aspartato compound

U.S. Pat. No. 4,431,666 Bulten et al—platinum(IV) diamine

U.S. Pat. No. 4,466,924 Verbeck et al—platinum(IV) diamine complex

U.S. Pat. No. 4,482,569 Bulten et al—platinum(IV) complex

The grounds for novelty or patentability of the present process lies in the utilization of a hexachloro salt $K_2PtCl_6$ instead of the $K_2PtCl_4$ utilized in previous processes.

In the reaction Scheme I above, platinum reactant, preferably $K_2PtCl_6$ is used, although a commercially usable alkali metal such as sodium or lithium may also be utilized soluble as the acid. As to the diamine reactant, the present process is fashioned towards products which will be compatible with prior results for anticancer therapy but the process will operate utilizing ethylene diamine or isomeric 1-amino-methyl-2- aminocyclohexane, etc.

DETAILED DESCRIPTION OF THE INVENTION

The process claimed in this invention, shown above in Scheme I, involves a novel, single step synthesis of tetrachloro-1,2-diaminocyclohexane platinum (IV) complex 4. In this process an equimolar mixture of 1,2-diaminocyclohexane dihydrochloride 5 and $K_2PtCl_6$ is refluxed in water. The product, substantially pure (>98% by HPLC) tetrachloro-1,2-diaminocyclohexane platinum (IV) complex 4 is isolated as a yellow crystalline material after concentration of the reaction mixture. The process of the present invention has been carried out starting with trans (d,l)-1,2-diaminocyclohexane hexane ·2HCl, and the product is isolated in 80% yield. The process is equally applicable for the preparation of cis, trans-d, and trans-l -1,2-DACH Pt (IV) complexes starting from appropriate 1,2-diaminocyclohexanes.

The hexachloroplatinate described in the above process is commercially available (for example, Alfa Research Chemicals, Danvers, MA) and the pure isomeric 1,2-diaminocyclohexanes are prepared utilizing published procedure (for example, Kidani, et al, *Chem. Lett.*, 1976, 123, 4,169,846; Whiteney, *J. Org. Chem.*, 45:4214, 1980).

Choice of the Platinum Precursors

Although both $K_2PtCl_4$ (competing process) and $K_2PtCl_6$ (present process) are commercially available, it is much more economical to prepare these intermediates starting from metallic platinum. The well-known literature procedure involves oxidation of Pt metal with a mixture of concentrated $HNO_3$ and concentrated $HCl$. This reaction (Scheme II below) produces $H_2PtCl_6$ 7. Compound 7 is treated with KCl to produce $K_2PtCl_6$ 6. In order to obtain $K_2PtCl_4$ 2, it is necessary to reduce compound 6 with hydrazine hydrate or a similar reducing agent.

Scheme II

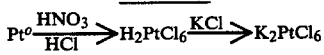

-continued
Scheme II $$K_2PtCl_6 \xrightarrow{NH_2NH_2} K_2PtCl_4$$
$$\quad\;\; 6 \qquad\qquad\qquad\;\; 2$$

In this process either compound 7 or compound 6 can be used, whereas a competing procedure utilizes compound 2. Thus, the present process saves at least one step and avoids using toxic reducing agent such as hydrazine.

Choice of Diamine Precursors

Known procedures use essentially the same published procedures to obtain the pure isomers of 1,2-diaminocyclohexane. The present process utilizes the dihydrochloride salts of these amines, whereas the known process uses the diamines in their free base form. The hydrochloride salts of these amines are highly stable crystalline solids, whereas the free bases are air-sensitive (reactive with atmospheric $CO_2$) liquids. In Kidani's process of separation of the cis/trans isomers (Kidani and Sato, Chem. Lett, 1976, 123) the intermediate Ni complexes are decomposed with acid and the amines are isolated in the salt form. The trans 1,2-diaminocyclohexane is first isolated as the dihydrochloride, and then the free base is generated from this salt. This last step involves neutralization of the salt with sodium hydroxide, extraction with benzene (for 8 hrs) and finally distillation to purify the liquid free base. There is a substantial loss of the product during this process. This present process avoids this last step and utilizes the salt form of the diamine.

Kidani's Process of Separation of Isomers

[Structural diagrams showing cis/trans diaminocyclohexane reacting with NiCl₂ to form cis and trans Ni complexes, then treatment with HCl to give trans-d,l dihydrochloride salt (5), then NaOH treatment to give trans-d,l free base (1).]

Reaction Between the Pt Moiety and the Diamine

Competing processes involve two steps. In the first step care must be taken to exclude atmospheric $CO_2$ from the reaction medium and involves isolation and purification of the intermediate. In the second step chlorine gas must be bubbled while the reaction mixture is at a high temperature (up to 100° C.). In contrast, the present process involves refluxing a mixture of the precursors in water to produce the final product. There is no need to protect the reaction mixture from atmospheric $CO_2$ and no need to use the toxic chlorine gas.

EXAMPLE

The following example describes the process for trans d,1 complex.

A mixture of trans (d,l) DACH-2HCl (0.4114 g, 2.2 mmol) and $K_2PtCl_6$ (0.9720 g, 2 mmol) in 50 mL of water were heated to reflux under stirring. At the end of 18 hrs, the yellow solution was cooled to room temperature, concentrated to about 30 mL, and placed in an ice-bath for 2 hrs. The precipitated, crystalline material was filtered and washed with about 10 mL of water. The combined filtrates were evaporated under reduced pressure to dryness, suspended in about 10 mL of water, and filtered. The solid was washed with 10 mL of ice-cold water, combined with the solid obtained in the first filtration, washed with ether, and air dried. Total weight of the solid, 0.718 g (79.6%). Purity >98% by HPLC.

Physical properties (trans d,l) complex:

(1) Melting point: 319–324 (d), turned black.

(2) Elemental analysis: Calculated for $C_6H_{14}N_2PtCl_4$·0.5$H_2O$: C, 15.66; H, 3.29; Cl, 30.82; N, 6.09; Pt, 42.40. Observed: C, 15.86; H, 3.24; Cl, 30.79; N, 6.19; and Pt, 42.27.

(3) TLC: Silica gel, 2—prOH—$H_2O$—HCOOH (20:5:1). The compound moved as a single spot (Rf=0.64).

(4) IR (K Br): 3450, 3140, 3060, 2920, 1550, 1150, 1120, 1050 and 1000 $cm^{-1}$.

(5) $^1$H-NMR (DMSO-$d_6$): 7.76–6.60 (br, 4H, $NH_2$) 3.20 (s, 1H, $H_2O$); 300–1000 (br, 10H, ring $CH_2$).

(6) Solubility: 6.0–7.5 mg/mL in water.

In the following claims, alkali metal = Na, K, Li and H.

I claim:

1. A method of preparing tetrachlorodiamine cyclohexane platinum (IV) ($PtCl_4^=$) and isomeric complexes by reacting 1,2-diaminocyclohexane in the form of dihydrohalides with an alkali metal or hydrogen chloroplatinate.

2. The method of claim 1 wherein alkali metal hexachloroplatinate is potassium hexachloroplatinate.

3. The method according to claim 1 of producing isomeric tetrachloro cyclohexane platinum (IV) ($PtCl_4^=$) complexes selected from the group consisting of cis, trans d,l, trans l, and trans d.

4. A method of preparing tetrachlorodiamine cyclohexane platinum (IV) ($PtCl_4^=$) and isomeric complexes by reacting a diamine selected from the group consisting of 1,2-diaminocyclohexane in the form of dihydrohalides with an equimolar amount of an alkali metal or hydrogen chloroplatinate wherein the 1,2-diaminocyclohexane is utilized in about 1:1 hexachloroplatinate, subjected to heating at reflux temperature for 12–24 hours in aqueous solvent and cooled and filtered.

5. The method of claim 4 wherein alkali metal hexachloroplatinate is potassium hexachloroplatinate.

6. The method of claim 4 of producing isomeric tetrachlorocyclohexane platinum (IV) ($PtCl_4^=$) complexes selected from the group consisting of cis, trans d,l, trans l, and trans d.

* * * * *